United States Patent [19]

Parker et al.

[11] 4,341,470

[45] Jul. 27, 1982

[54] ATOMIC ABSORPTION SPECTROSCOPY

[75] Inventors: Clive Parker, Mount Waverly; Antony Pearl, Park Orchards, both of Australia

[73] Assignee: Varian Associates, Inc., Palo Alto, Calif.

[21] Appl. No.: 810,232

[22] Filed: Jun. 22, 1977

Related U.S. Application Data

[63] Continuation of Ser. No. 376,498, Jul. 5, 1973, abandoned, which is a continuation of Ser. No. 208,772, Dec. 16, 1971, abandoned.

[30] Foreign Application Priority Data

Jan. 5, 1971 [AU] Australia ............................... 364371

[51] Int. Cl.$^3$ ........................ G01J 3/42; G01N 21/72; G01N 21/74
[52] U.S. Cl. ................................... 356/307; 356/312; 356/315
[58] Field of Search ........................ 356/312, 315, 307

[56] References Cited

U.S. PATENT DOCUMENTS

3,513,381  5/1970  Happer ............................ 324/0.5 A
3,676,004  7/1972  Prugger et al. ...................... 356/87

FOREIGN PATENT DOCUMENTS

918878  2/1963  United Kingdom .................. 356/85

OTHER PUBLICATIONS

Koizumi et al., *Analytical Chemistry*, vol. 47, No. 9, Aug. 1975, pp. 1679-1682.
Koizumi et al., *Analytical Chemistry*, vol. 48, No. 8, Jul. 1976, pp. 1178-1182.
Koizumi et al., *Spectrochimica Acta*, vol. 31 B, 1976, pp. 237-255.
Koizumi et al., *Spectrochimica Acta*, vol. 31 B, 1976, pp. 523-535.
McLaughlin, *Science*, vol. 174, Oct. 1971, pp. 404-407.
Hendrikx-Jongerius et al., *Analytica Chimica Acta*, vol. 87, No. 2, 1976, pp. 259-271.
Dawson et al., *Analyst*, vol. 101, Apr. 1976, pp. 315-316.
Stephens et al., *Talanta*, vol. 22, 1975, pp. 655-658.
Hollander et al., *Combustion and Flame*, vol. 13, No. 1, Feb. 1969, pp. 63-70.
van Heek, *Spectrochimica Acta, Part B, Atomic Spectroscopy*, vol. 25 B, No. 2, Feb. 1970, pp. 107-109.
West et al., *Analytica Chimica Acta*, vol. 45, Mar. 1969, pp. 27-41.
Wood, *Physical Optics*, New York, The Macmillan Company, 1911, pp. 530-547.
Chapman et al., *Journal of Physics B, Atomic and Molecular Physics*, vol. 3, No. 1, Jan. 1970, pp. 72-83.
Series, *Journal of Physics B, Atomic and Molecular Physics*, vol. 3, No. 1, Jan. 1970, pp. 84-97.
Dodd et al., *Journal of Physics B, Atomic and Molecular Physics*, vol. 3, No. 2, Feb. 1970.
Gough, *Journal of Physics B, Atomic and Molecular Physics*, vol. 3, No. 12, Dec. 1970, pp. 1636-1945.

*Primary Examiner*—F. L. Evans
*Attorney, Agent, or Firm*—Stanley Z. Cole; Gerald M. Fisher

[57] ABSTRACT

A method and apparatus for carrying out atomic spectroscopy, and particularly atomic absorption and atomic fluorescence spectroscopy. The method involves passing the emission spectrum of a light source through an atomized sample, changing the relationship between a selected emission line of the emission spectrum and a corresponding absorption line of the atoms of interest and measuring the absorption of that emission line by the sample before and after the aforementioned change in relationship. The change in emission and absorption line relationship can be effected by application of the Zeeman Effect, Stark Effect, or Doppler Effect. The apparatus, in one form, includes an electro-magnet operative to apply a magnetic field to the atomized sample and thereby cause splitting and shifting of the aforementioned absorption line, and the magnet is modulated to effect periodic variation of the spectral line relationship.

30 Claims, 10 Drawing Figures

ATOMIC ABSORPTION SPECTROSCOPY

This is a continuation of application Ser. No. 376,498 filed July 5, 1973, now abandoned, which is a continuation of application Ser. No. 208,772 filed Dec. 16, 1971, now abandoned.

This invention relates to a method and means for carrying out atomic spectroscopy such as used for the analytical determination of various elements, and is applicable to atomic absorption spectroscopy (AAS) atomic fluorescence spectroscopy (AFS) or any other form of spectroscopy where a source emitting discrete lines is used and there is absorption of the line radiation by a substance with a narrow absorption profile (a narrow absorption line width). As a matter of convenience however, the invention will be hereinafter particularly described in relation to AAS.

In AAS the concentration of a chemical element in a sample is determined by measuring the degree to which atoms of the element absorb light of a wave-length which characterize those atoms. Usually, the light is generated by a discharge lamp and the sample to be analyzed is in the form of a solution which is dissociated in any one of several ways to provide a cloud of atoms in the light path. For example, the cloud of atoms may be produced by spraying the sample solution into a flame or by depositing a small amount of the sample solution on a heated filament, rod, or other nonflame device. The light passing through the sample region is received by a suitable detector and the degree of light absorption is measured. Theoretically, the absorption of the light source radiation by atoms of the dissociated sample is a measure of the concentration of the element of interest in the solution, but in practice some of that radiation can also be absorbed by species within the dissociated sample other than the atoms of interest. Such additional absorption is generally termed non-atomic absorption (NAA), and can be substantial under some circumstances so that correction is necessary to obtain an accurate measure of the concentration of the element of interest.

A further problem arises out of the fact that the degree of NAA generally varies with time, which variation is a major source of noise known as flame absorption noise, and consequently it is desirable to find a way to minimize or cancel that variation.

Prior attempts to overcome the foregoing difficulties have mainly relied on the fact that NAA occurs over a relatively wide band of wave-lengths as compared to the narrow wave-length line in which atomic absorption occurs. The most favoured prior method involves using a continuum light source such as a hydrogen or tungsten lamp and measuring the NAA over its broad spectral band in the wave-length vicinity of the atomic absorption line. The NAA measured with use of the continuum light source is compared with the absorption measured with the usual narrow line discharge lamp, and suitable correction is made to the lastmentioned measurement in an endeavour to determine the actual atomic absorption.

The foregoing method suffers several disadvantages as follows.

(a) An error in the final determination results from the assumption that over the band of wave-lengths concerned in the NAA measured, the contribution of the still present atomic absorption can be ignored.

(b) It is essential for the continuum light source lamp and the usual narrow band discharge lamp to be positioned so that identical light paths through the sample region are achieved, and this constraint introduces considerable optical and mechanical difficulties.

(c) Either lamp can drift in intensity so that the system is further complicated by the need to monitor the two light sources.

(d) In order to maximize the signal to (flame) noise ratio it is necessary to continuously alternate between non-atomic absorption and atomic absorption measurements, and this practice is difficult because of the need to periodically switch two light beams along identical paths through the sample region.

With the foregoing disadvantages of the conventional method in mind, it was postulated that it should be possible to use a single light source and to modulate atomic absorption without affecting non-atomic absorption and thereby provide a means of electronically discriminating between atomic absorption and non-atomic absorption. In accordance with the invention, that is achieved by varying the wave-length of the wave-length of the absorption line of the atoms of interest, so as to change the overlap of the wave-length ranges of the emitted light and the absorbed atoms. The wave-length variation may be periodic or otherwise—for example, it could be effected in a series of discrete steps—and it will be convenient to hereinafter refer to that variation as "modulation", regardless of how it is effected.

For the purposes of this specification, the expression "wave-length profile" is to be understood as the narrow range of wave-lengths distributed around a discrete spectral line, or in other words the intensity distribution of wave-lengths about a spectral line.

It is a principal object of the present invention to provide a method for carrying out atomic spectroscopy with a greater degree of accuracy than hitherto possible. It is a further object of the invention to provide means suitable for performing the improved method.

Still a further object of the invention is to provide a method of atomic spectrum analysis utilizing a single light source, in which a magnetic field is applied to the sample under investigation so as to vary the relationship between a selected spectral line of the light source emission spectrum and a corresponding spectral line of the absorption spectrum of the sample, and the energy from the selected emission line which is absorbed by the sample is determined before and during application of the magnetic field. Yet another object of the invention is to provide a method as described in the immediately preceding passage, but in which the wave-length profile relationship is varied by application of either the Doppler Effect or the Stark Effect.

As previously mentioned, the invention is applicable to fluorescence spectroscopy as well as absorption spectroscopy, but as a matter of convenience it will be described mainly in relation to the latter type of analysis. With that in mind, the expressions "measuring the energy absorbed", "determining the energy absorbed", and similar expressions of like import as used throughout this specification are to be understood as embracing situations in which the absorption of energy (light intensity) is measured directly as in atomic absorption spectroscopy, or indirectly such as by measuring the intensity of re-radiation by the absorbing atoms of the sample, as in atomic fluorescence spectroscopy.

The following description refers in more detail to these essential features and further optional features of the invention. To facilitate an understanding of the invention, reference is made to the accompanying drawings where these features are illustrated in preferred form. It is to be understood however, that the essential and optional features of the invention are not limited to the specific forms of these features as shown in the drawings.

The method of the present invention is similar to the prior art methods in that it makes use of a broad band nature of NAA as a basis for distinguishing between NAA and atomic absorption. It is unique however, in that it can be carried out using a single light source and in that the wave-length of a corresponding line of the atoms of interest, is varied to change the overlap of the wave-length ranges of the emitted light and the absorbing atoms. The variation in overlap can be periodic or otherwise, and it will generally be convenient to refer to that variation as modulation of the wave-length ranges or of wave-length profiles.

As previously mentioned, in atomic absorption spectrophotometry, the light source emits light having a narrow range of wave-lengths—e.g. generally in the range 0.01 to 0.1 Angstroms—and the atoms in the sample region absorb only narrow wave-length ranges. Furthermore, those atoms absorb light from the source only if the two aforementioned wave-length ranges overlap, so that if the wave-length line is shifted to reduce the degree of overlap, there will be a corresponding reduction in the amount of absorption. Non-atomic absorption however, occurs over a comparatively large wave-length range so that it will not be affected by such a shift in wave-length. Thus, periodic fluctuation of each wave-length results in a corresponding fluctuation of the intensity of the light received by the detector and that variation in the intensity can be taken as a measure of the concentration of absorbing atoms in the sample region.

If the foregoing wave-length change is applied with suitable frequency (for example 30 to 100 times per second), fluctuations in non-atomic absorption due to fluctuations in the carrying medium (e.g., flame etc.) can be reduced. In addition, fluctuations in the intensity of light from the source may be effectively cancelled if those fluctuations are slow compared with the periodic alteration of the wave-length. However, this is a source of error if the source lamp is modulated by a magnetic field because intensity changes are induced at the modulation frequency.

By use of such a wave-length modulation the non-atomic absorption is automatically eliminated and without approximation by the read-out electronics associated with the detector. The problem of aligning lamps and/or mirrors, and of providing an independent monitoring of intensities of two lamps, does not exist in the method of this invention as it does in prior methods. Furthermore, there is no loss of light due to multiple refractions or reflections of light other than those used by a normal (basic) system.

The desired wave-length modulation may be obtained in any one of several ways. For example, use could be made of the Doppler Effect—i.e., the wave-length of light emitted by a moving system is a function of the velocity of the emitter in relation to the receiver. Doppler wave-length modulation may be effected by means of supersonic nozzles, atomic beam sources, or any other configuration in which the velocity of an absorber can be controlled and directed.

Another possible method would be to split and shift the spectral lines by means of an electric field, thereby making use of the Stark Effect. This could be done by means of specially designed lamps. In this particular method a strong electric field applied to the absorbing atoms will cause the spectral lines to be split into two or more components, depending on the atoms concerned and the direction of the field relative to the direction of propagation of the light beam.

It is preferred however, to produce the desired wave-length modulation through use of the Zeeman Effect—i.e., magnetic field splitting of the spectral line. The degree of splitting is directly proportional to the applied magnetic field, and this method can take any one of several forms. If the magnetic field is applied to absorbing atom along the line of observation, in the normal Zeeman Effect, two symmetrically displaced Zeeman lines will result and they are circularly polarized in opposite directions. If on the other hand, the magnetic field is applied at right angles to the direction of observation, in the normal Zeeman Effect, the original spectral line profile, either a source profile or an absorber profile will be split into three Zeeman components—one central undisplaced line called the Pi polarized line and two lines symmetrically displaced on either side of the zero field position called the Sigma polarized lines. The central undisplaced line is linearly polarized parallel to the field direction, whereas the displaced components are linearly polarized in a direction perpendicular to the applied field.

The most direct method of Zeeman modulation is to modulate the magnetic field, and the following possibilities are available:

1. Modulation of a longitudinal field, such as one produced by a solenoid.
2. Modulation or rotation of a transverse field—a fixed linear polaroid oriented to eliminate the central undisplaced line, will give an enhancement of sensitivity.
3. A fixed transverse field from a permanent or electromagnet with an oscillating, rotating, or modulated polaroid which can alternately select the lines polarized perpendicular to each other.

The net effect of each of the foregoing possibilities is substantially the same when the normal Zeeman Effect obtains. That is, alternate phases of the modulating cycle give an undisplaced line which is absorbed with the same sensitivity as in normal atomic absorption, followed by a phase in which the undisplaced line is replaced by two symmetrically displaced lines resulting in a reduced atomic absorption. In the anomolous Zeeman Effect the picture is somewhat more complicated and method 3 may not be as effective e.g. if the undisplaced component is absent.

In the methods proposed, relying on Stark or Zeeman Effect, the different lines resulting from the splitting are polarized differently from each other and consequently may be examined separately by the interposition of suitable polarizing fibers. This may be a practical advantage in increasing the sensitivity of the measurement of change in absorption.

Figure 1:
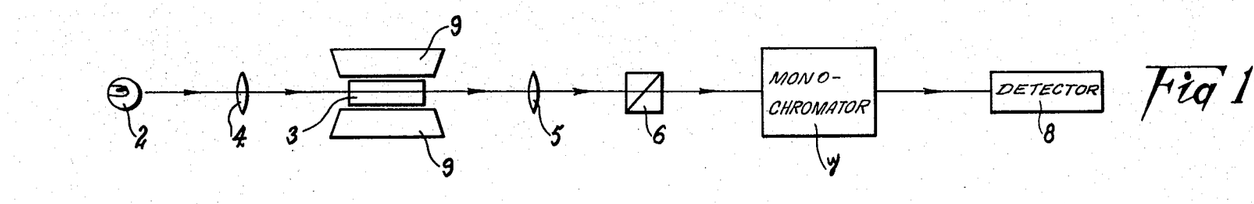
FIG. 1 is a schematic view of one possible apparatus arrangement for carrying out a method according to the invention.

FIG. 1 provides a diagrammatic illustration of the main components of one form of the apparatus for carrying out the foregoing method. In that particular embodiment, a light source 2 such as a hollow cathode lamp is arranged to direct its emission spectrum through an atomized sample formed by an atomizing device 3, which is preferably a burner and nebulizer arrangement such as used in prior conventional apparatus, although other devices such as a carbon rod atomizer may be used. A collimator lens 4 is located in the path of the emission spectrum on the inlet side of the atomizer device 3, and a focusing lens 5 is located in that path on the outlet side of the device 3—which arrangement is typical of conventional apparatus. The beam of light focused by lens 5 passes in turn through a polarizer 6 and monochromator 7, to a detector 8.

In this particular embodiment, a magnet 9 is arranged to create a transverse magnetic field in that region of the atomized sample through which the emission spectrum passes, and the magnet 9 is modulated in a manner hereinafter described in detail so as to obtain the desired change in overlap between the selected emission line and the corresponding absorption line of the sample. The polarizer 6 is preferably fixed linear polarizer of a known kind arranged to eliminate the central undisplaced component of the spectral line of interest—i.e., the central component resulting from splitting of that line under the influence of the magnetic field—thereby increasing the sensitivity of the apparatus. The monochromator 7 isolates the spectral line of interest for transmission to the detector 8, which is responsive to the intensity of the transmitted spectral line.

Figure 2:
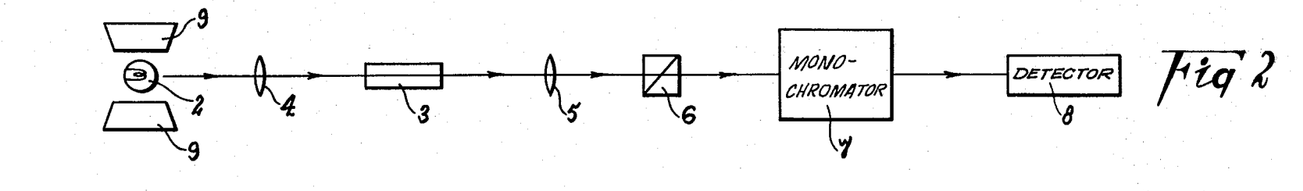
FIG. 2 is a schematic view of an apparatus applying a magnetic field to the source lamp.

FIG. 2 illustrates prior art apparatus wherein the magnet 9 is applied to the light source resulting in splitting of the emission spectrum of the source.

It is to be appreciated that the FIG. 1 embodiment is open to substantial variation. For example, the magnet 9 may be energized continuously, and the polarizer 6 modulated. In addition, the magnetic field may be applied longitudinally to rather than transversely to the light beam.

Figure 3:
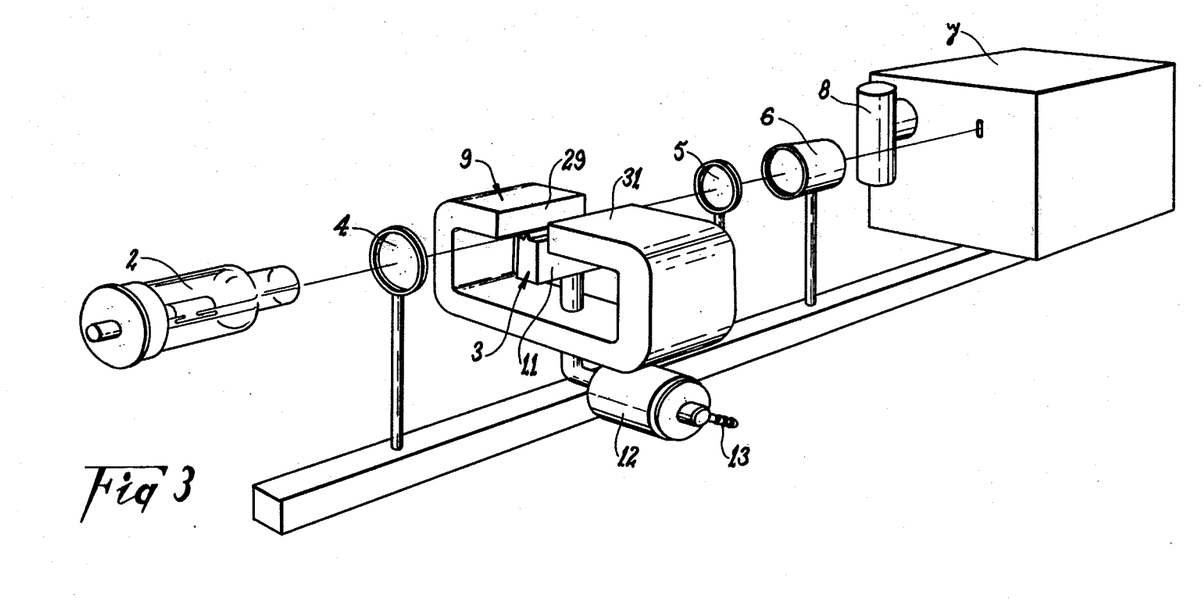
FIG. 3 is a semi-diagrammatic perspective view of apparatus according to FIG. 1, parts being omitted for convenience of illustration.

The FIG. 1 embodiment is presently preferred, and the following description of the operation of the apparatus will be directed primarily to that embodiment. FIG. 3 provides a slightly more detailed view of the FIG. 1 embodiment, and in particular shows the atomizer device 3 as comprising a burner 11 and connected nebulizer and spray chamber assembly 12. The chamber 12 is connected by way of nipple 13 to a sample supply source (not shown).

The apparatus preferably includes a "lock-in" detection system such as is also used in conventional atomic absorption instruments, so as to enable the light intensity from the lamp 2 to be measured without interference from the light emitted from the burner flame. The lamp or light source 2 is intensity modulated by a square-wave (at say 100 cycles per second) and the detector electronics is tuned in frequency and phase to the lamp wave form. In this way the detector 8 "sees" the light from the hollow cathode lamp 2 but does not "see" the unwanted flame emission light which is unmodulated (d.c.). The non-atomic absorption may be registered on another channel.

Figure 5:
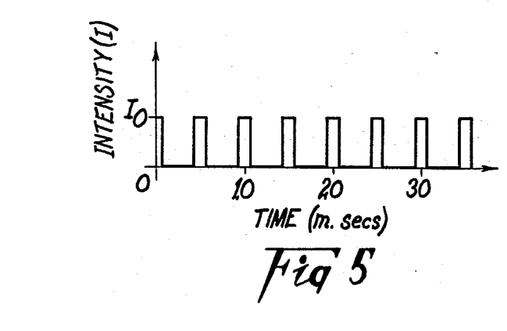
FIG. 5 is a representation of the wave-form of the lamp as used in the FIG. 4 embodiment.
Figure 6:
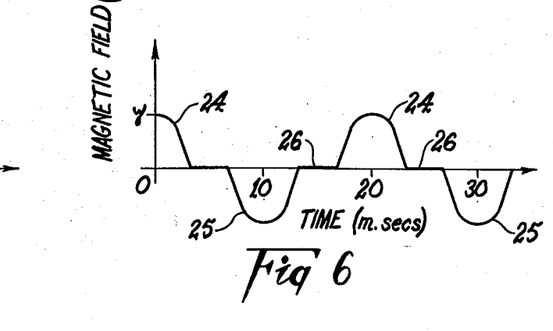
FIG. 6 is a representation of the wave-form of the magnetic field created by the magnet of the apparatus according to FIG. 4.

FIG. 5 provides a diagrammatic illustration of the wave form of the light source 2. The magnetic field wave form used in a presently preferred embodiment, is derived from a sine-wave and is substantially as shown in FIG. 6, but that wave form is not to be regarded as essential to performance of the invention.

Figure 4:
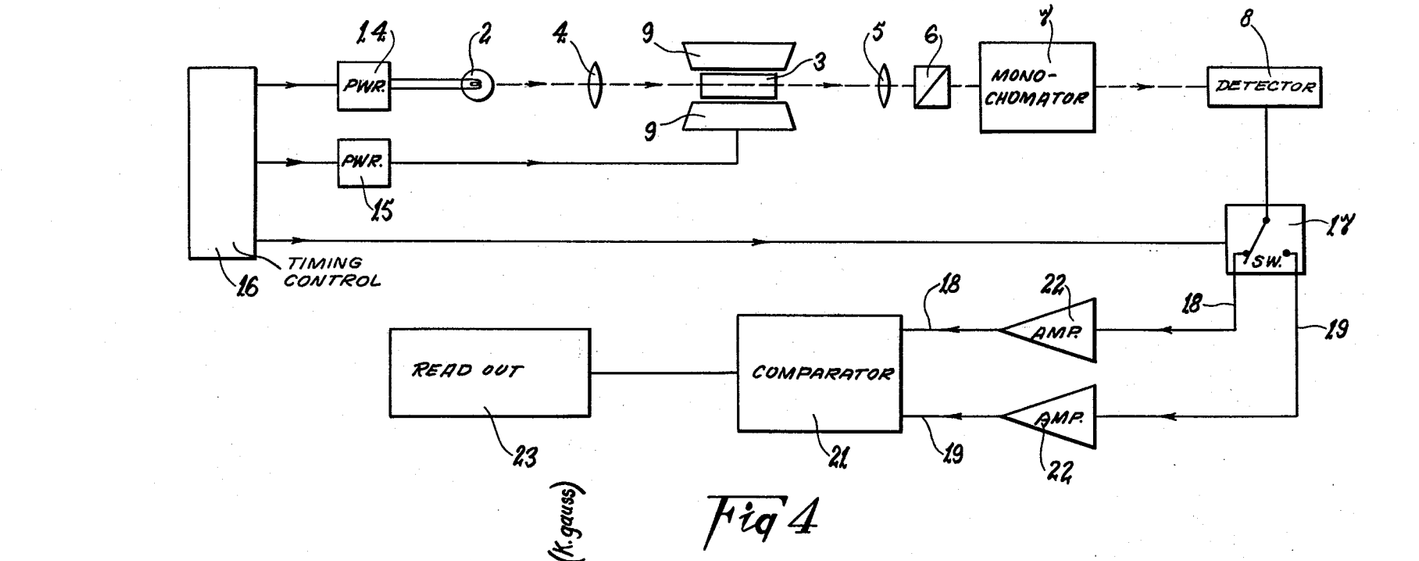
FIG. 4 is a schematic view of the electrical circuit as applied to one embodiment of the apparatus according to FIG. 3.

One particular electrical circuit for the FIG. 1 embodiment is shown diagrammatically in FIG. 4. The lamp 2 and electro-magnet 9 are operatively connected to respective power supplies 14 and 15, and those power supplies are controlled through a timing sequence control 16 which will be hereinafter described in more detail. The control 16 is also connected to a switch 17 arranged to receive a signal from the detector 8, and, according to its position, to relay that signal along either channel 18 or 19 to a sub-circuit or analogue circuit 21 arranged to compare the respective signals transmitted along channels 18 and 19 and produce a resultant signal equivalent to the equation minus $Log_{10} I/I_B$. In the foregoing equation I and $I_B$ are representative of the intensities of the emission line transmitted through the atomized sample and received by the detector 8 when the magnet 9 is not energized and when the magnet is energized and is producing a field of maximum magnitude respectively. The signals transmitted along channels 18 and 19 are proportional to the respective light intensities received by the detector 8, and the Logarithm of the ratio of the two signals gives the "magnetic absorbance" which is a measure of the analyte concentration.

An amplifier 22 is preferably provided in each channel 18 and 19, and the sub-circuit 21 is arranged according to conventional electronics techniques. The signal resulting from the sub-circuit 21 is transmitted to an appropriate read-out device 23 which includes transducers or other means to enable the signal to be recorded in an appropriate manner. The signal may be recorded on a chart or dial, or by digital read-out mechanism.

The control 16 is adapted to cause energization and de-energization of the lamp 2 at the appropriate times during the magnetic field duty cycle, and in the preferred arrangement the lamp 2 is switched on when the magnetic field is zero and is switched off as the magnitude of the magnetic field increases. When the magnetic field has attained its maximum value, the lamp is again switched on. The switch 17 is regulated by the control 16 so that it connects the detector 8 to channel 18 or 19 according to whether the magnetic field is at zero or maximum value respectively.

The circuit of the control 16 includes a silicon controlled rectifier (not shown) or other semi-conductor switch connected to the magnet power source 15 so as to energize the magnet 9 a short time after the A.C. mains voltage has reached a peak in one direction, de-energize the magnet 9 when the current reverses, and re-energize the magnet 9 after a suitable time delay before the next voltage reversal. Any known triggering circuit may be employed to effect such controlled switching of the rectifier.

In FIG. 6, the upper section 24 of the distorted sine-wave curve represents the first part of a work cycle of the magnet 9, and the lower section 25 of the curve represents the second or re-energization part of that cycle. The flat section 26 represents the time delay or de-energization period of the magnet 9, and that delay provides an opportunity to measure the intensity of the beam received by the detector 8 whilst the condition of the beam remains substantially static. A further advantage of this particular magnetic field wave form is that the power requirements of the magnet 9 are low.

Figure 7:
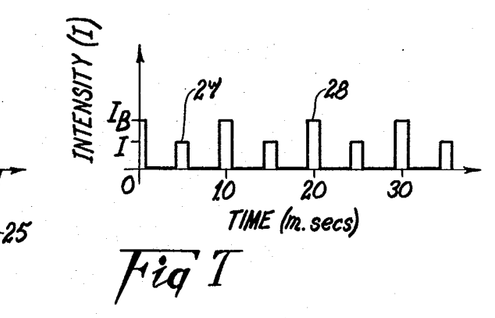
FIG. 7 is a representation of the wave-form of light as seen by the detector of the apparatus according to FIG. 4.

FIG. 7 provides a diagrammatic representation of the wave form of the light seen by the detector 8 in the presence of absorbing atoms, and resulting from the lamp and magnetic field wave forms shown in FIGS. 5 and 6. The low peaks 27 represent the light beam intensity I previously discussed, which is received by the detector 8 when the magnetic field is zero, and the high peaks 28 represent the intensity $I_B$ which is received by the detector 8 when the magnetic field is at maximum magnitude.

In applying the magnet 9 to the sample as in the preferred embodiment described, it is desirable to locate the magnet pole ends 29 and 31 (see FIGS. 3 and 8) close to the atomized sample, but that involves the risk of the burner flame 32 (FIG. 8) contacting the pole ends 29 and 31 with consequent overheating of the magnet 9. The arrangement diagrammatically shown in FIG. 8 overcomes that problem by providing an air passage 33 between each pole end 29 and 31 and the adjacent side of the burner body 11. In practice, it is found that a flow of air is induced through each of the passages 33 over the pole ends 29 and 31, and that flow provides a barrier such as to prevent direct contact between the flame 32 and the pole ends 29 and 31.

Figure 8:
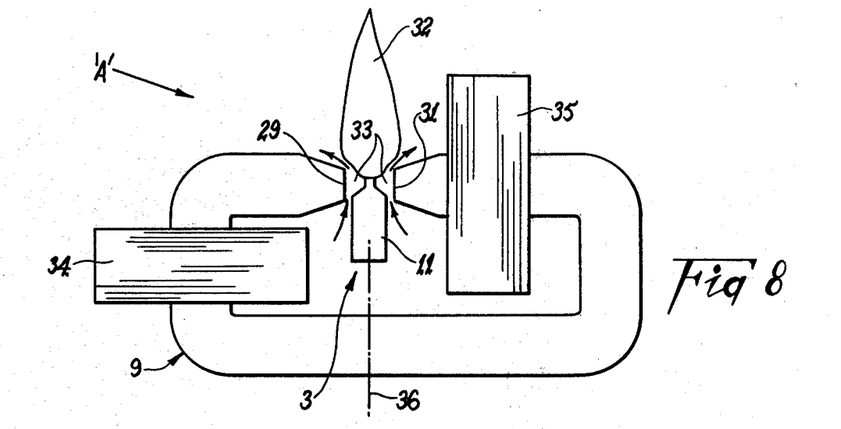
FIG. 8 is a semi-diagrammatic view of one possible magnet arrangement for use in the apparatus of FIG. 3 or 4.

The arrangement of the coils 34 and 35 of the electro magnet 9 shown in FIG. 8, is also novel in that it enables the magnet 9 to operate at a fairly high level of efficiency and also allows a relatively clear line of vision of the sample region (base of the flame 32) in the direction of arrow A. Maximum magnet efficiency would be achieved with both coils 34 and 35 disposed with their windings transverse to the respective pole end portions of the magnet 9, but that arrangement would make it difficult to see the sample region. The FIG. 8 arrangement presents an acceptable compromise in providing a clear line of vision without a substantial sacrifice in efficiency of the magnet 9.

It is also preferred that the magnet 9 and the burner 3 be mounted for rotation around an axis 36 (FIG. 8) so as to allow adjustment of the disposition of the atomized sample relative to the light path of the lamp 2. The magnet 9 and burner 3 are preferably secured against relative movement so that they move as a unit about the axis 36.

Figure 9:
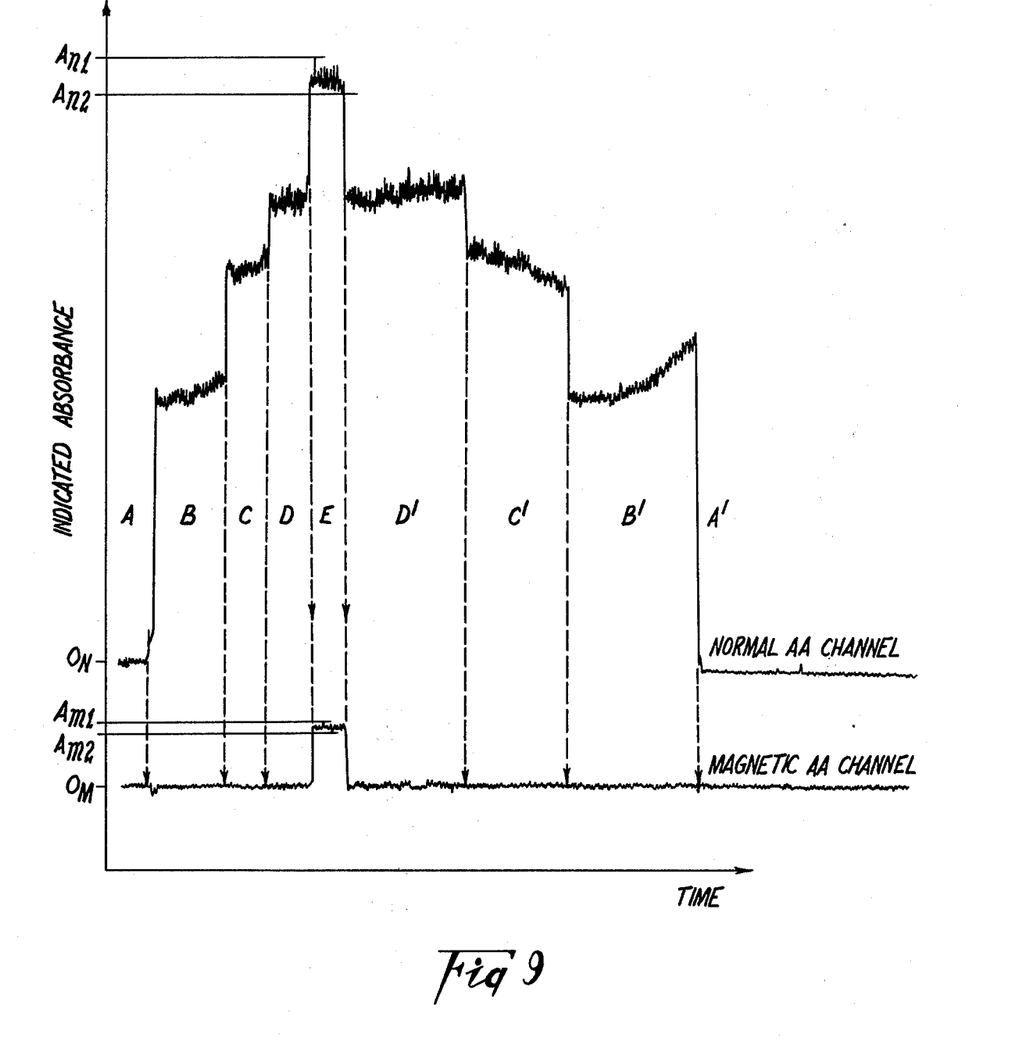
FIG. 9 is a graphical representation of the absorbance signals recorded during analytical determination of an arsenic sample using both the conventional atomic absorption technique and a method according to the present invention.

Experiments conducted to data strongly suggest that the method of the present invention is applicable to all elements accessible to conventional atomic absorption spectroscopy. FIG. 9 shows an arsenic determination as recorded by both the conventional atomic absorption technique and a method according to the present invention in which a magnetic field was applied to the atomized sample—i.e., the particular method employed involved use of apparatus substantially as shown in FIG. 3. The two separate determinations recorded by the graph shown in FIG. 9, were made by using the same light source and the same sample. Arsenic determination is usually complicated because of non-atomic absorption effects in both the flame and the matrix accompanying the sample.

In effecting the determination using the normal atomic absorption technique, the lamp 2 was energized to produce an absorbance signal which was recorded as the line On. During the relevant time period A, there was no flame or sample in the path of the light source emission spectrum. The flame was ignited and some absorption occurred as recorded by the upper line extending over the time period B. Water was then aspirated into the flame during time period C, and this produced a further increase in the indicated absorbance as is clearly shown by the graph. A blank, comprising a solution substantially identical to that forming the sample but excluding arsenic—i.e., the sample matrix—was introduced into the flame in place of the water in an attempt to simulate the unwanted absorption expected to be recorded when using the actual sample, and a further increase in the indicated absorbance resulted.

The actual sample was introduced during time period E, and the difference in the absorbance recorded during periods D and E is taken as a measure of the atomic absorption. All absorption signals occurring during time period B, C and D are spurious unwanted signals and are a source of error, and it will be observed that during each time period B, C, D and E there is a substantial fluctuation in the signal which results from flame noise—e.g., during period E the signal fluctuated between upper and lower levels $A_{n1}$ and $A_{n2}$ respectively.

Simply for the purpose of illustration, each of the steps preceding consideration of the sample, was repeated in reverse order during time periods D', C', B' and A', as shown by FIG. 9. During normal analysis procedure the step occurring time period D' would be omitted, but water would be aspirated as in period C' so as to clean the system preparatory to analysis of a new sample.

Turning now to the signals recorded on the magnetic atomic absorption channel, the base line (i.e., the line of zero absorbance) of those signals is represented by the line Om. During the detection cycle represented by the time periods A, B, C, D, E, D', C', B' and A', the steps described in relation to the normal atomic absorption channel were carried out, but absorbance was recorded only during the critical period E so that non-atomic absorption signals were rejected. It will be further observed that the fluctuation in absorbance signals is far less pronounced than in the normal atomic absorption technique, so that there is relatively little difference between the upper and lower levels of atomic absorption recorded —i.e., $A_{m1}$ and $A_{m2}$ respectively. The magnetic field used during the determination represented by FIG. 9 was 100 cycles per second and had a peak of 7 K. gauss.

Figure 10:
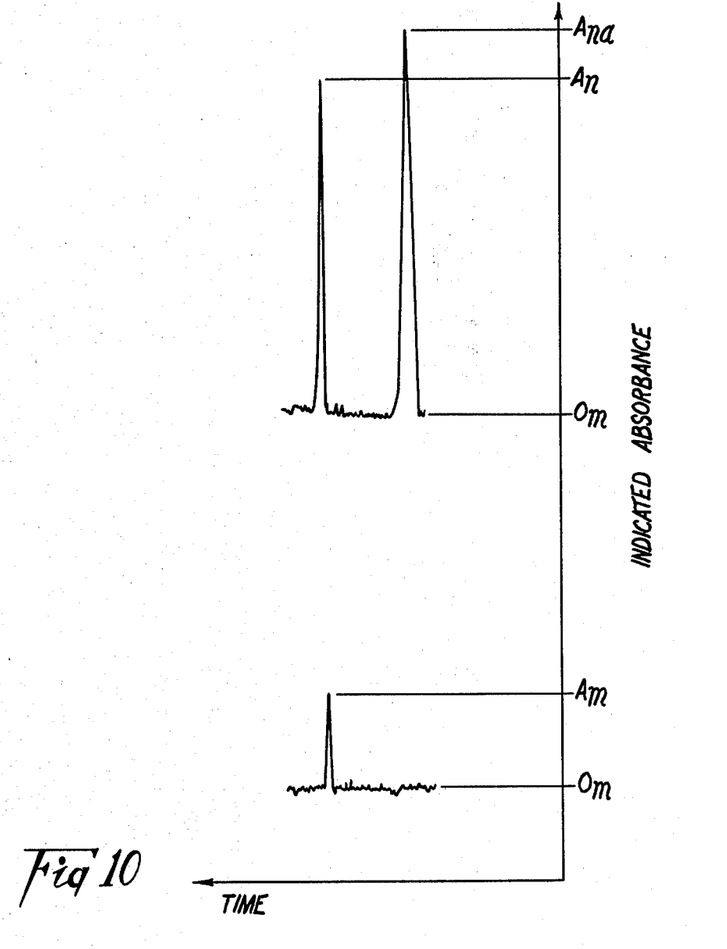
FIG. 10 is a graphical representation similar to FIG. 9 but relating to a lead in oil sample atomized by a carbon rod filament.

FIG. 10 is a graphic representation similar to FIG. 9 in that it shows a comparison of signals recorded by conventional atomic absorption and magnetic atomic absorption according to the invention, but dealing with a determination of lead in oil. A further difference is that the atomizer means used in that determination comprised a carbon rod filament as distinct from a flame atomizer as used for the determination of FIG. 9. The upper graph represents the signals recorded on the normal atomic absorption channel, as is also the case in FIG. 9, and the lower graph represents the signals recorded on the magnetic atomic absorption channel.

Considering the first peak on the normal atomic absorption graph, which has its apex at level $A_{na}$, that resulted from an "ashing" step during which the carbon rod was heated to burn-off unwanted chemicals that could interfere with the final reading. Consequently, that first peak represents non-atomic absorption, and it is relevant that during the "ashing" period, the base line $O_m$ recorded by the magnetic atomic absorption channel remained substantially constant. The atomic absorption recorded on the normal atomic absorption channel is represented by the second peak having its apex at level $A_n$.

Non-atomic absorption presents a serious problem in apparatus using carbon rod atomizers, and the time resolution of the atomic and non-atomic peaks is not often as pronounced as shown in FIG. 10. Thus, it will be seen that use of a method or apparatus according to the present invention effectively overcomes that problem.

Experiments have demonstrated that for some elements 90% modulation of the absorption is possible using the Zeeman Effect with a magnetic field in the region of 6 K gauss. The following serves to illustrate how a method according to the invention can be used to obtain accurate determination of atomic absorption.

Mathematical Description of the Method

If the light from the light source, incident on the flame has an intensity $I_o$, the transmitted intensity received by the detector is given by $$I = I_o \exp.[-(\beta KC + N(c,t))] \quad (1)$$

where $\beta KC$ is the atomic absorbance for a sample concentration C, K is the absorption coefficient for the atomic species in the flame and $\beta$ is an instrumental parameter relating the concentration of the element in the sample solution to the measured absorbance in the flame. N (c,t) is the non-atomic absorbance which may or may not depend on the sample concentration and may be time varying.

Equation (1) is the basic equation of conventional AA.

If a magnetic field of strength B gauss is applied either to the light source or to the absorbance medium, the factor K in the above equation is decreased to a value $K_B$ depending on the relative widths of the emission and absorption profiles so that the transmitted light intensity increases to $I_B$ where $$I_B = I_o' \exp.[-(K_B C + N(c,t))] \quad (2)$$

the non-atomic term in the exponent being unaffected by the magnetic field. $I_o'$ is the incident intensity in the magnetic field and $$\alpha = I_o / I_o'$$

is assumed to remain constant; $\alpha = 1$ for the field on the flame. If we take the ratio (electronically) or otherwise) $I/I_B$ we obtain $$\frac{I}{I_B} = \alpha e^{-(K - K_B)C} \quad (3)$$

provided the ratio is taken in a time short compared with variations in $I_o$ and N (c,t).

The ratio $I/I_B$ can be used to measure the atomic concentration 'C' with an effective "magnetic" absorbance $(K-K_B)C$.

Note that the concentration given by the equation $$C = \frac{1}{K} \log_e \frac{I_o}{I}$$

is only valid if N (c,t) = 0 in equation (1) and that the value of C depends on $I_o$ the incident intensity from the lamp.

In the system according to the present invention, the concentration is given by $$C = \frac{1}{(K - K_B)} \log_e \left( \frac{I_B}{I} \right)$$

which is independent of N (c,t) and $I_o$ provided the ratio $I/I_B$ is taken rapidly compared with the rates of change of these parameters.

Thus to sum up, the proposed system should enable measurements to be made which will automatically eliminate errors arising from
 (1) Lamp drift
 (2) Non-atomic absorption and with the appropriate electronics reduce the influence of
 (1) Lamp noise
 (2) Flame noise.

An additional feature of the Zeeman type method according to the invention is that adjustment of the strength of the magnetic field enables the absorbance to be changed for a given concentration. Thus, if a sample has an excessively high concentration such as to be not adapted to give a reasonable transmitted intensity, the magnetic field can be modified to cause a corresponding reduction in absorbance. It therefore follows that simple manipulation of associated apparatus is only necessary to increase the dynamic range of that apparatus, and this is a feature not found in apparatus for carrying out prior methods.

The foregoing can perhaps be best explained with reference to the preceding mathematical description. In the mathematical description, absorbance in normal atomic absorption is defined as $\beta KC$ and is the strength of a signal for a given concentration. If the concentration is high enough to give an absorbance of more than 2 then it is not usually possible to make a measurement as 99% of the incident light has been absorbed. Thus conventional AA as a measurement technique is severely limited in dynamic range—i.e., the range of concentrations that can be conveniently measured.

In magnetic AA, the magnetic absorbance is defined in the preceding mathematical description as $\beta(K-K_B)C$. If $\beta(K-K_B)C$ were greater than 2, it is possible by arranging the sequence of lamp intensity measurements, to reduce it by only making intensity measurements at high fields, thus $(K-K_B)C$ would be reduced to $(K_{B1}-K_{B2})C$ where $K_{B1} \approx K_{B2}$ because $B_1 \approx B_2$ and hence $(K_{B1}-K_{B2})C$ can be made small. Thus by sequencing the light intensity measurements so that instead of a maximum field—zero field sequence, we have a maximum field—near maximum field sequence, it is possible to measure higher concentrations than can be measured by conventional AA. In essence the absorption of the atoms is being measured when the atoms are most transparent to the detuned incident radiation.

It has been suggested that the modulating means—e.g., magnetic field—can be applied to the light source as shown in FIG. 2 rather than than atomized sample as particularly described in relation to FIGS. 1, 3, 4 and 8, and whilst that remains a valid possibility, it is presently thought that best results will be usually obtained by modulating the atoms of the sample. That is, considering employment of the Zeeman Effect for example, application of the magnetic field to the atomized sample results in an automatic correction for lamp drift. In addition, application of the magnetic field to the atomized sample avoids difficulties in calibration that will normally result from modulating the lamp. By way of explanation, application of the magnetic field to the lamp tends to introduce non-linearity into the calibration (i.e., the absorption versus concentration graph), whereas application of the magnetic field to the atomized sample provides for linear calibration which is much simpler to deal with.

In order for the atomic absorption to be linear in calibration it is necessary for the light source to emit atomic spectral lines of the element to be determined, that are narrow compared with the absorption line to be measured. Application of the magnetic field to the lamp would in effect cause broadening of the emission spectral lines thereby creating a less favourable condition, whereas application of the magnetic field to the atomized sample causes broadening of the absorption line so enhancing the desired relationship between the emission lines and the absorption line.

It will be understood from the foregoing that application of the magnetic field, or other modulating means to the atomized sample achieves the dual function of background correction and light source monitoring.

In practice, some magnetic modulation of the atomic emission will occur when the magnetic field is applied to the atomized sample, and in the embodiment of FIGS. 1, 3, 4 and 8 as previously described, electronic correction of that modulation can be effected by looking at the emission at or near zero and maximum field phases of the cycle.

Both the method and apparatus particularly described in this specification involve the use of a single light source, but it is possible to embody the invention in a method and apparatus involving the use of two separate light sources.

It will be clear from the foregoing description that the present invention provides an extremely simple and yet effective method and means for conducting atomic spectroscopy. In particular, the invention overcomes the inaccuracies in readout resulting from non-atomic absorption and lamp drift in conventional single beam atomic absorption.

Finally, it is to be understood that various alterations, modifications and/or additions may be introduced into the methods, and constructions and arrangements of parts previously described without departing from the spirit or ambit of the invention.

Having now described our invention, what we claim as new and desire to secure by Letters Patent is:

1. Atomic spectrum analysis apparatus for elements exhibiting an anomalous Zeeman splitting characteristic including a light source made from an element exhibiting an anomalous Zeeman splitting characteristic, atomizing means for directing a cloud of an atomized sample into the path of a beam of light emitted by said source, photoelectric detection means for detecting and measuring the intensity of a selected spectral line of the atomic emission spectrum of said light source after said line has passed through said atomized sample, and transverse magnetic field means operative upon said atomized sample to cause anomalous Zeeman splitting of the absorption profile of said cloud of atoms, means to cause said photoelectric detection means to sense the effect of said splitting in the relationship between said selected emission line and a corresponding absorption line of said atomized sample, wherein said means to cause said photoelectric detection means to sense the effect of said splitting includes means to modulate said magnetic field.

2. Atomic spectrum analysis apparatus including a light source providing radiation derived from an element exhibiting an anomalous Zeeman splitting characteristic, atomizing means for directing a cloud of an atomized sample into the path of a beam of light emitted by said source, photoelectric detection means for detecting and measuring the intensity of a selected spectral line of the atomic emission spectrum of said light source after said line has passed through said atomized sample, and magnetic field means operative upon said atomized sample to cause anomalous Zeeman splitting of the absorption profile of said cloud of atoms, means to cause said photoelectric detection means to sense the effect of said splitting in the relationship between said selected emission line and a corresponding anomalous absorption line of said atomized sample, wherein said means to cause said photoelectric detection means to sense the effect of said splitting includes means to alternately pass different portions of said transmitted beam to said detector.

3. The apparatus of claim 2 wherein said magnetic field means comprising an electromagnet having pole faces separated by an air gap between which faces, in operation, said cloud of atomized sample is disposed, said poles of said electromagnet being displaced from said atomizing means to provide an ingress and egress for cooling gases to said pole faces.

4. Atomic spectrum analysis apparatus including, a light source, atomizing means for directing a cloud of an atomized sample into the path of a beam of light emitted by said source, photoelectric detection means for detecting and measuring the intensity of a selected spectral line of the atomic emission spectrum of said light source after said line has passed through said atomized sample, an magnetic field means operative upon said atomized sample to induce a change in the relationship between said selected emission line and a corresponding absorption line of said atomized sample, means connected to said photoelectric detection means for determining the concentration of atoms in said cloud of atoms as a function of absorption of said beam of light, including control means wherein said light source and said magnetic field means are both actuated responsive to said control means which is operative to energize said light source when said magnetic field is de-energized, to de-energize said light source when said magnetic field is energized, and to re-energize said light source when said magnetic field is substantially at maximum magnitude.

5. Apparatus according to claim 4, wherein said control means includes a switch device through which power is supplied to said magnetic field means, and a triggering circuit operatively connected to said switch device and responsive to phase changes in the supply of said power so as to effect a predetermined time delay between de-energization and re-energization of said magnetic field means.

6. Atomic spectrum analysis apparatus including, a light source, atomizing means for directing a cloud of an atomized sample into the path of a beam of light emitted by said source, photoelectric detection means for detecting and measuring the intensity of a selected spectral line of the atomic emission spectrum of said light source after said line has passed through said atomized sample, and magnetic field means operative upon said atomized sample to induce a change in the relationship between said selected emission line and a corresponding absorption line of said atomized sample, means connected to said photoelectric detection means for determining the concentration of atoms in said cloud of atoms as a function of absorption of said beam of light, wherein said magnetic field means includes an electromagnet having its two pole ends and associated coils disposed on opposite sides respectively of a region above said atomizing means wherein said cloud of the atomized sample will be formed, one said coil being arranged with its windings extending transverse to the respective end portion of the electromagnet, and the other said coil being arranged with a portion of its windings extending substantially parallel to the respective end portion of the electromagnet.

7. Apparatus according to claim 6, wherein said atomizing means includes an elongated burner body located between the pole end faces of said electromagnet so that each said end face overlaps a respective side face of said burner body, and a space is defined between each said side face of the burner body and the overlapping end face of the electromagnet so as to form an air passage, said air passage being arranged so that during operation of said burner a flow of air is induced over each said end face of the electromagnet so as to prevent direct contact of the burner flame with said end faces and thereby guard against overheating of said electromagnet.

8. Atomic spectrum analysis apparatus including, a light source, atomizing means for directing a cloud of an atomized sample into the path of a beam of light emitted by said source, photoelectric detection means for detecting and measuring the intensity of a selected spectral line of the atomic emission spectrum of said light source after said line has passed through said atomized sample, and magnetic field means operative upon said atomized sample to induce a change in the relationship between said selected emission line and a corresponding absorption line of said atomized sample, means connected to said photoelectric detection means for determining the concentration of atoms in said cloud of atoms as a function of absorption of said beam of light, wherein said magnetic field means and said atomizing means are attached against relative movement and are rotatably mounted so as to enable alteration of the relationship between said cloud of the atomized sample and said path of said beam from said light source.

9. Atomic spectrum analysis apparatus including, a light source, carbon element atomizing means for directing a cloud of an atomized sample into the path of a beam of light emitted by said source, photoelectric detection means for detecting and measuring the intensity of a selected spectral line of the atomic emission spectrum of said light source after said line has passed through said atomized sample, and magnetic field means operative upon said atomized sample to induce a change in the relationship between said selected emission line and a corresponding absorption line of said atomized sample, means connected to said photoelectric detection means for determining the concentration of atoms in said cloud of atoms as a function of absorption of said beam of light, wherein said magnetic field means comprising an electromagnet having pole faces separated by an air gap between which faces, in operation, said cloud of atomized sample is disposed, said poles of said electromagnet being displaced from said atomizing means to provide an ingress and egress for cooling gases to said pole faces, including first means to periodically change the intensity of light emitted from said light source, second means to cause said magnetic field means to periodically change the relationship between said selected emission line and a corresponding line of said atomized sample, control means for causing the frequency of each said first and second means to be synchronously related.

10. The apparatus of claim 9 wherein said control means includes means for causing said light source to be on when the magnetic field is a first predetermined value and said light source to be switched off when the magnetic field exceeds a predetermined second value, and where said light source is switched on again when said magnetic field value reaches a third predetermined value.

11. The apparatus of claim 10 wherein said first predetermined value is substantially zero, and said second predetermined value is the maximum magnetic field value.

12. The apparatus of claim 10 wherein said first predetermined value is greater than zero in order to increase the dynamic range of concentration measurements.

13. Atomic spectrum analysis apparatus including, a light source, atomizing means for directing a cloud of an atomized sample into the path of a beam of light emitted by said source, photoelectric detection means for detecting and measuring the intensity of a selected spectral line of the atomic emission spectrum of said light source after said line has passed through said atomized sample, and magnetic field means operative upon said atomized sample to induce a change in the relationship between said selected emission line and a corresponding absorption line of said atomized sample means connected to said photoelectric detection means for determining the concentration of atoms in said cloud of atoms as a function of absorption of said beam of light wherein said magnetic field means includes a first coil having a first axis and a second coil having a second axis, said first and second coil being disposed about a core of magnetic material having a pole face on each end of said core, said magnetic core extending between said first and second coil, said pole faces being substantially parallel and separated by an air gap, said second axis of said second coil and said first axis of said first coil forming a plane which is perpendicular to said pole faces.

14. The apparatus of claim 13 wherein said first axis of said first coil is perpendicular to said pole faces and said second axis of said second coil is parallel to said pole faces.

15. Atomic spectrum analysis apparatus including, a hollow cathode lamp light source, atomizing means for directing a cloud of an atomized sample into the path of a beam of light emitted by said source, photoelectric detection means for detecting and measuring the intensity of a selected spectral line of the atomic emission spectrum of said light source after said line has passed through said atomized sample to induce a change in the relationship between said selected emission line and a corresponding absorption line of said atomized sample, means connected to said photoelectric detection means for determining the concentration of atoms in said cloud of atoms as a function of absorption of said beam of light, including control means wherein said light source and said magnetic field means are both actuated responsive to said control means which is operative to energize said light source when said magnetic field is de-energized, to de-energize said light source when said magnetic field is energized and to re-energize said light source when said magnetic field is substantially at maximum magnitude.

16. Apparatus according to claim 15, wherein said control means includes a switch device through which power is supplied to said magnetic field means, and a triggering circuit operatively connected to said switch device and responsive to phase changes in the supply of said power so as to effect a predetermined time delay between de-energization and re-energization of said magnetic field means.

17. Atomic spectrum analysis apparatus including, a hollow cathode lamp light source, atomizing means for directing a cloud of an atomized sample into the path of a beam of light emitted by said source, photoelectric detection means for detecting and measuring the intensity of a selected spectral line of the atomic emission spectrum of said light source after said line has passed through said atomized sample, and magnetic field means operative upon said atomized sample, to induce a change in the relationship between said selected emission line and a corresponding absorption line of said atomized sample, means connected to said photoelectric detection means for determining the concentration of atoms in said cloud of atoms as a function of absorption of said beam of light, wherein said magnetic field means includes an electromagnet having its two pole ends and associated coils disposed on opposite sides respectively of a region above said atomizing means wherein said cloud of the atomized sample will be formed, one said coil being arranged with its windings extending transverse to the respective end portion of the electromagnet, and the other said coil being arranged with its windings extending substantially parallel to the respective end portion of the electromagnet.

18. Atomic spectrum analysis apparatus including, a hollow cathode lamp light source, carbon element atomizing means for directing a cloud of an atomized sample into the path of a beam of light emitted by said source, photoelectric detection means for detecting and measuring the intensity of a selected spectral line of the atomic emission spectrum of said light source after said line has passed through said atomized sample, magnetic field means operative upon said atomized sample to induce a change in the relationship between said selected emission line and a corresponding absorption line of said atomized sample, means connected to said photoelectric detection means for determining the concentration of atoms in said cloud of atoms as a function of absorption of said beam of light, wherein said magnetic field means comprises an electromagnet having pole faces separated by an air gap between which faces, in operation, said cloud of atomized sample is disposed, said poles of said electromagnet being displaced from said atomizing means to provide an ingress and egress for cooling gases to said pole faces, first means to periodically change the intensity of light emitted from said light source, second means to cause said magnetic field means to periodically change the relationship between said selected emission line and a corresponding line of said atomized sample, control means for causing the frequency of each said first and second means to be synchronously related.

19. Atomic spectrum analysis apparatus including, a light source, atomizing means for directing a cloud of an atomized sample into the path of a beam of light emitted by said source, photoelectric detection means for detecting and measuring the intensity of a selected spectral line of the atomic emission spectrum of said light source after said line has passed through said atomized sample, magnetic field means operative upon said atomized sample to induce a change in the relationship between said selected emission line and a corresponding absorption line of said atomized sample, means connected to said photoelectric detection means for determining the concentration of atoms in said cloud of atoms as a function of absorption of said beam of light, first means to periodically change the intensity of light emitted from said light source, second means to cause said magnetic field means to periodically change the relationship between said selected emission line and a corresponding line of said atomized sample, and control means for causing the frequency of each said first and second means to be synchronously related.

20. Improved apparatus for atomic absorption spectroscopy of a selected element exhibiting an anomalous Zeeman characteristic;

a radiation source for providing a probe beam, said radiation source comprising said selected element which exhibits an anomalous Zeeman splitting characteristic;

an atomizer adapted to receive a sample to be analyzed for the concentration of said selected element in said sample, said atomizer providing, in operation, a cloud of atoms including atoms of said sample and background absorbers, if any, into said probe beam;

magnet means for providing a magnetic field substantially transverse to said probe beam, said magnetic field being applied, in operation, to said atomized atoms for causing said atoms to split;

means for selecting a first portion of said probe beam radiation transmitted through said atomizer, which first portion is reduced in intensity due to absorption by said cloud of atoms and background absorbers;

means for selecting a second portion of said probe beam radiation transmitted through said atomizer, which said second portion is reduced in intensity due to absorption by said background absorbers only;

means for photoelectrically detecting and measuring the intensity of said selected first and second portions of said transmitted probe beam; and means connected to said means for photoelectrically detecting and measuring said first and second selected portions of said transmitted beam for determining a measure of the concentration of atoms of said selected element in a sample introduced into said atomizer as a function of the intensity of said first and second portion of said transmitted beam.

21. Apparatus according to claim 20 wherein said means for selecting said first portion of said probe beam radiation includes a polarizer between said radiation source and said photoelectric detection means.

22. Apparatus according to claim 21 wherein said polarizer also comprises the means for selecting the second portion of said probe beam and wherein said means for selecting said first portion and second portions of said probe beam radiation includes means for modulating said polarizer to pass said first portion of said probe beam radiation to said photoelectric detection means for a first period of time and to pass said second portion of said probe beam radiation to said photoelectric detection means for a second period of time.

23. A method of atomic spectrum analysis of elements exhibiting an anomalous Zeeman splitting characteristic including the steps of: dissociating a sample into its atomic elements; directing a beam of light from a light source made from an element exhibiting an anomalous Zeeman splitting characteristic through said atomized sample, the wave lengths of the atomic emission spectrum of said light source including the absorption wave lengths of a particular element sought to be detected in said sample, selecting a spectral line of said emission spectrum that corresponds to an absorption line of said atomized sample and therefore has a wave length profile which overlaps the wave length profile of said absorption line; applying a periodic transverse magnetic field to said atomized sample thereby inducing a change in at least one of said wave length profiles so that the degree of overlap of said profiles alternates between a plurality of values; photoelectrically detecting the energy from said selected emission line transmitted by said sample at said plurality of values of overlap; and electrically comparing the energy transmitted at one of said values with the energy transmitted at the other said value; generating a signal derived from said comparison, and providing an indication of said generated signal.

24. A method of atomic spectrum analysis of elements exhibiting an anomalous Zeeman splitting characteristic including the steps of: dissociating a sample into its atomic elements; directing a beam of light from a light source made from an element exhibiting an anomalous Zeeman splitting characteristic through said atomized sample, the wave lengths of the atomic emission spectrum of said light source including the absorption wave lengths of a particular element sought to be detected in said sample; selecting a spectral line of said emission spectrum corresponding to an absorption line of said atomized sample and which has a wave length profile which overlaps the wave length profile of said absorption line; applying a transverse magnetic field to said atomized sample to cause lateral displacement of components of said absorption spectral line; passing that part of said emission spectrum of said light source which passes through said atomized sample through a polarizer to select transmitted perpendicularly polarized components of said light source line; measuring the intensity of said transmitted perpendicularly polarized components respectively; and comparing said intensities to provide a measure of concentration of atoms of said element corrected for absorption of said emission spectrum by said sample.

25. Atomic spectrum analysis apparatus including, a light source emitting a resonance line of an element exhibiting an anomalous Zeeman line splitting characteristic, atomizing means for directing a cloud of an atomized sample including said element exhibiting an anomalous Zeeman characteristic into the path of a beam of light emitted by said source, photoelectric detection means for detecting and measuring the intensity of a selected spectral line of the atomic emission spectrum of said light source after said line has passed through said atomized sample, a magnetic field means operative upon said atomized sample to induce a change in the relationship between said selected emission line and a corresponding absorption line of said atomized sample, means connected to said photoelectric detection means for determining the concentration of atoms in said cloud of atoms as a function of absorption of said beam of light, and a control means wherein said light source and said magnetic field means are both responsive to said control means which is operative to energize said light source when said magnetic field is deenergized and to energize said light source when said magnetic field is substantially at maximum magnitude.

26. Atomic absorption analysis apparatus including, a light source made from an element exhibiting an anomalous Zeeman splitting characteristic, atomizing means for directing a cloud of sample atoms exhibiting said anomalous splitting characteristic into said beam of light emitted from said source, means for detecting and measuring the intensity of said beam after transmission through said cloud of atoms, and means for determining the concentration of atoms in said cloud of atoms as a function of absorption of said beam of light, magnetic field means operative upon said atomized sample to induce a change in relationship between a selected emission line profile of said light source and a corresponding line profile of said atomized sample atoms, and control means to cause said magnetic field means to modulate said magnetic field and to cause said means for determining the concentration to compare the absorption when the magnetic field is near zero to the absorption when the magnetic field is at a non-zero value.

27. Apparatus for atomic absorption including:
a light source made from an element exhibiting an anomalous Zeeman splitting characteristic for providing a probe beam;
atomizing means for directing a cloud of sample atoms exhibiting said anomalous Zeeman splitting characteristic into a beam derived from said light source;

means for applying a magnetic field to said cloud of sample atoms to cause said atoms to exhibit their anomalous Zeeman splitting characteristic;

means for selecting and detecting the transmitted intensity of a first and second portion of said beam which has passed through said cloud of atoms, said first portion being reduced by absorption due to background and said second portion being reduced by absorption due to both background absorption and said sample atoms absorption;

means for determining the concentration of said anomalous characteristic atoms in said cloud of atoms as a function of said first and second portion by obtaining a comparison between said first and second portion of said beam.

28. The apparatus of claim 27 wherein said means for applying a magnetic field provides a magnetic field transverse to said probe beam.

29. The apparatus of claim 27, wherein said means for selecting and detecting the transmitted intensity of a first and second portion of said beam includes means to modulate the magnetic field, means to photoelectrically detect transmitted light and means to substantially block the Pi component of said probe beam from reaching said photoelectric detector means.

30. The apparatus of claim 27, wherein said means for selecting and detecting the transmitted intensity of a first and second portion of said beam includes photoelectric detector means and variable polarizer means for selectively passing the Pi polarized or the Sigma polarized portion of said probe beam.

* * * * *